US00PP10432P

United States Patent [19]

Kientzler

[11] Patent Number: Plant 10,432

[45] Date of Patent: Jun. 2, 1998

[54] NEW GUINEA IMPATIENS PLANT 'KIPAS'

[75] Inventor: Ludwig Kientzler, Gensingen, Germany

[73] Assignee: Paul Ecke Ranch, Inc. Encinitas, Calif.

[21] Appl. No.: 797,288

[22] Filed: Feb. 7, 1997

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Kipas', but marketed under 'Pascua', characterized by its flat and rounded light purple-colored flowers; freely flowering habit; outwardly spreading, mounded and rounded growth habit; and dark green, slightly glossy, non-variegated foliage.

2 Drawing Sheets

The present invention relates to a new and distinct cultivar of New Guinea Impatiens plant, botanically known as *Impatiens hawkeri*, which is to be internationally registered as 'Kipas'. It is anticipated that the plant will be marketed under the synonym 'Pascua'. Hereinafter the disclosed plant will be referred to as 'Pascua'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as L787 as the male, or pollen parent, with the proprietary seedling selection identified as P242 as the female, or seed patent. The cultivar Pascua was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of 'Pascua'. These characteristics in combination distinguish 'Pascua' as a new and distinct cultivar:

1. Flat and rounded light purple-colored flowers.
2. Freely flowering habit.
3. Outwardly spreading, mounded and rounded growth habit.
4. Dark green, slightly glossy, non-variegated foliage.

The new New Guinea Impatiens is similar in flower color to the New Guinea Impatiens cultivars Aruba (disclosed in U.S. Plant Pat. No. 8,456) and Bora-Bora (disclosed in U.S. Plant Pat. No. 8,421). However in side-by-side comparisons in Encinitas, Calif., under commercial practice, plants of the new New Guinea Impatiens differed from plants of the cultivars 'Aruba' and 'Bora-Bora' in the following characteristics:

1. Plants of the new New Guinea Impatiens have larger leaves than plants of the cultivars 'Aruba' 'Bora-Bora'.
2. Plants of the new New Guinea Impatiens are different in leaf and petiole color than plants of the cultivars 'Aruba' and 'Bora-Bora'.
3. Plants of the new New Guinea Impatiens are more freely flowering than plants of the cultivars 'Aruba' and 'Bora-Bora'.
4. Flowers of plants of the new New Guinea Impatiens are rounded whereas flowers of plants of the cultivars 'Aruba' and 'Bora-Bora' are star-shaped.

5. Plants of the new New Guinea Impatiens have larger flowers than plants of the cultivars 'Aruba' and 'Bora-Bora'.

A detailed comparison of plants of the New Guinea Impatiens and the cltivars 'Bora-Bora' and 'Aruba' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Pascua'.

The second photograph comprises a close-up view of typical flowers and leaves of the varieties 'Aruba' (top left of photo), 'Bora-Bora' (top right of photo) and 'Pascua' (bottom of photo).

The flower and foliage colors in the photographs may differ from the actual colors due to light reflectance.

The cultivar 'Pascua' has not been observed under all possible environmental conditions. The phenotype may vary somewhat with variations in environment such as temperature and light intensity, without, however, any variance in genotype. The following observations, measurements and comparisons describe plants grown 10-cm pots i Encinitas, Calif., under commercial practice in a fiberglass-covered greenhouse with day temperatures ranging from 23 to 29C and night temperatures ranging from 16 to 18C with light levels averaging 3,000 footcandles.

In the following description, color references are made to The Royal Horticultural Society Colour Chart except where general terms of ordinary dictionary significance are used.

Classification:

*Botanical.*—*Impatiens hawkeri.*

*Commercial.*—New Guinea Impatiens 'Kipas', but marketed under 'Pascua'.

Parentage:

*Male parent.*—Proprietary seedling seection L787.

*Female parent.*—Proprietary seedling selection P242.

Propagation:

*Type cutting.*—Terminal cuttings.

*Time to initiate roots.*—About 15 days with 21C soil temperature.

Plant description:

*Plant form.*—Outwardly spreading, rounded and mounding.

*Growth habit.*—Vigorous. Moderate branching, dense and bushy growth. Suitable for 10 to 25-cm containers.

*Plant size.*—Height: About 20 cm. Width or spread: About 29 cm.

*Lateral branches.*—Quantity: About seven. Size: Length: About 15 cm. Diameter: 7 to 11 mm. Internode length: 5 to 6 cm. Color: Darker than 59A.

*Foliage description.*—Leaves simple, generally symmetrical, abundant, opposite or in whorls or three, horizontal to plant and flat in aspect. Size, largest leaves: Length: 12.5 to 13 cm. Width: About 4.8 cm. Shape: Ovate with acuminate apex, attenuate base and ciliate margin. Texture: Smooth, slightly glossy. Color: Young foliage, upper surface: 147A. Young foliage, lower surface: 59A. Fully expanded foliage, upper surface: Darker than 147A. Fully expanded foliage, lower surface: 59B/59C. Venation, upper surface: 60A. Venation, lower surface: 59A. Petiole: Size: Length: 3.5 to 4 cm. Diameter: About 5 mm. Color: 60A.

Flower description:

*Flower type and habit.*—Large light purple-colored flowers. Freely and continuously flowering. Flowers arise from leaf axils. Usually eight flowers per lateral branch. Flowers positioned at or just above the foliage and face upward or outward. Flowers flat and rounded. Flowers persistent.

*Flowering season.*—Year-round under greenhouse conditions. In the garden, flowering is continuous from spring until fall.

*Flower size.*—Length: About 7 cm. Width: About 7 cm. Depth: About 6 mm.

*Flower buds.*—Size: Length: About 2.7 cm. Diameter: About 1.2 cm. Shape: Ovoid. Color: 60A/80B.

*Petals.*—Quantity: Five. Size (largest petals): Length: Top Petal: About 3.2 cm. Middle petals: About 3.4 cm. Bottom petals: About 4 cm. Width: Top Petal: About 4.8 cm. Middle petals: About 3.6 cm. Bottom petals: About 4 cm. Sape: Cordate with emarginate apex, cuneate or obtuse base and entire margin. Texture: Velvety, smooth. Color: When opening, upper surface: Iridescent, 80B. When opening, lower surface: Iridescent, 80C. Fully opened, upper surface: Iridescent, slightly lighter than 80C with 66B at base. Fully opened, lower surface: Iridescent, 80C. Fading to: 80B/80C.

*Spur.*—Length: About 5.5 cm. Shape: Narrow and curved. Color: Proximal: 60B. Distal tip: 144A.

*Peduncles.*—Length: About 4.5 cm. Angle: Erect to slightly outward. Strength: Strong. Color: 144B with 60B stripes.

*Reproductive ograns.*—Androecium: Stamen number: Five, anthers fused, filaments free. Anther shape: Obovate. Anther size: 6 by 4mm. Anther color: Cream. Amount of pollen: Moderate. Pollen color: Creamy white. Gynoecium: Five-loculate fused. Stigma color: White. Gynoecium length: About 6 mm. Gynoecium color: 59A.

Disease resistance: Under commercial conditions, resistance nor susceptibility to pathogens has not been observed.

Seed development: Seed production is not usually observed.

CHART A

| CHARACTERISTIC | 'PASCUA' | 'ARUBA' | 'BORA-BORA' |
|---|---|---|---|
| LEAF LENGTH | 12.5 to 13 cm | 9 to 10.5 cm | About 9.5 cm |
| LEAF WIDTH | About 4.8 cm | 3.5 to 4 cm | 3.5 to 4 cm |
| LEAF COLOR, YOUNG, UPPER SURFACE | 147A | 147A | Darker than 146A |
| LEAF COLOR, YOUNG, LOWER SURFACE | 59A | Darker than 59A | 146B |
| LEAF COLOR, FULLY EXPANDED, UPPER SURFACE | Darker than 147A | 147A with dark red tones | 147A |
| LEAF COLOR, FULLY EXPANDED, LOWER SURFACE | 59B/59C | 185B | 146B |
| VENATION COLOR, UPPER SURFACE | 60A | 59A | 63B |
| VENATION COLOR, LOWER SURFACE | 59A | 60A | 63A |
| PETIOLE LENGTH | 3.5 to 4 cm | About 3 cm | 2.5 to 3 cm |
| PETIOLE COLOR | 60A | 59B | 63A |
| QUANTITY OF FLOWERS PER LATERAL STEM | About 8 | About 5 | About 5 |
| FLOWER SHAPE | Rounded | Star-shaped | Star-shaped |
| FLOWER LENGTH | About 7 cm | About 5.7 cm | About 6 cm |
| FLOWER WIDTH | About 7 cm | About 5.2 cm | About 6 cm |
| PETAL COLOR, WHEN OPENING, UPPER SURFACE | 80B | Redder than 80A, bluer than 74B | 80A |
| PETAL COLOR, WHEN OPENING, LOWER SURFACE | 80C | 74B | 80C |
| PETAL COLOR, OPENED, UPPER SURFACE | Lighter than 80B with 66B base | 80A with 74B base | 80A with lavender/white base |
| PETAL COLOR, OPENED, LOWER SURFACE | 80C | 80B | 80C |
| PETAL COLOR, FADING TO | 80B/80C | 80C | 80C |
| SPUR COLOR | 60B | 60A | 60A |

It is claimed:

1. A new and distinct cultivar of New Guinea Impatiens plant, as illustrated and described.

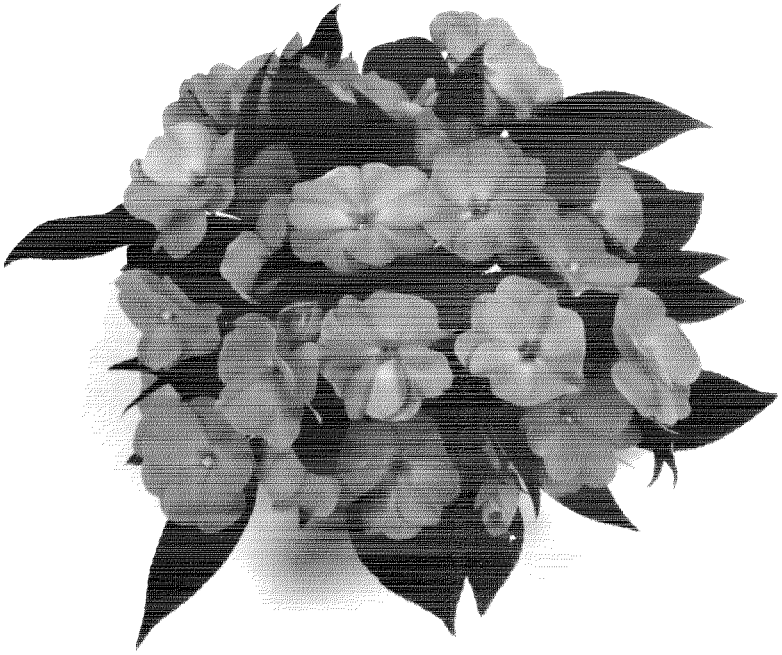

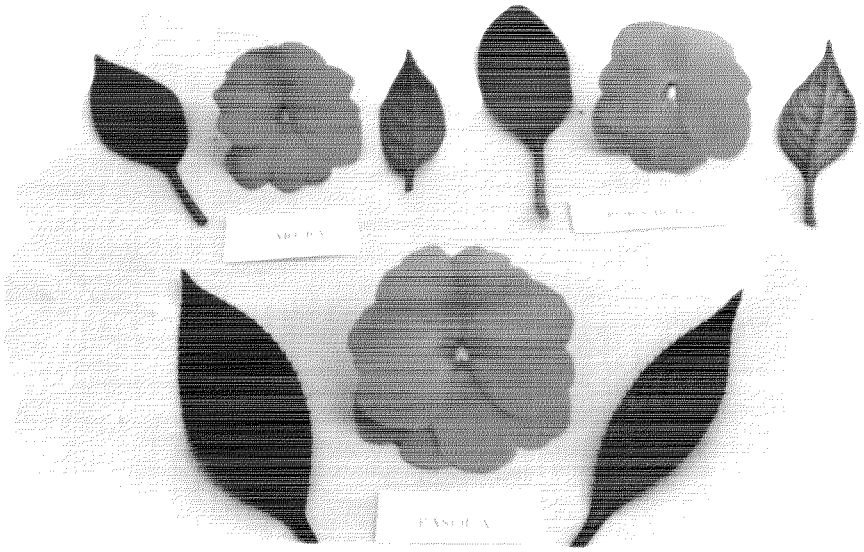

* * * * *